(12) United States Patent
Layton, Jr.

(10) Patent No.: US 8,523,826 B2
(45) Date of Patent: Sep. 3, 2013

(54) LUER-TYPE NEEDLE-FREE VALVE FITTING WITH BYPASS

(75) Inventor: Russell K. Layton, Jr., Acton, MA (US)

(73) Assignee: Cytyc Corporation, Marlborough, MA (US)

( * ) Notice: Subject to any disclaimer, the term of this patent is extended or adjusted under 35 U.S.C. 154(b) by 613 days.

(21) Appl. No.: 12/371,346

(22) Filed: Feb. 13, 2009

(65) Prior Publication Data

US 2010/0211020 A1    Aug. 19, 2010

(51) Int. Cl.
*A61M 5/315*    (2006.01)
*A61M 25/16*    (2006.01)
*A61M 25/18*    (2006.01)
*A61M 39/00*    (2006.01)
*A61M 39/10*    (2006.01)

(52) U.S. Cl.
USPC ........................................... 604/237; 604/533

(58) Field of Classification Search
USPC .............. 604/33, 167.03, 167.05, 236, 237, 604/247, 248, 249; 251/149, 149.1, 149.7, 251/149.8, 149.9
See application file for complete search history.

(56) References Cited

U.S. PATENT DOCUMENTS

| | | | |
|---|---|---|---|
| 3,192,949 A | 7/1965 | De See | |
| 3,385,301 A | 5/1968 | Harautuneian | |
| 3,570,484 A | 3/1971 | Steer | |
| 3,831,629 A | 8/1974 | Mackal | |
| 3,896,853 A * | 7/1975 | Bernhard | 137/614.05 |
| 3,986,508 A * | 10/1976 | Barrington | 604/411 |
| 4,160,383 A * | 7/1979 | Rauschenberger | 73/863.85 |
| 4,222,407 A | 9/1980 | Ruschke | |
| 4,246,932 A | 1/1981 | Raines | |
| 4,286,628 A | 9/1981 | Paradis et al. | |
| 4,310,017 A | 1/1982 | Raines | |
| 4,369,812 A | 1/1983 | Paradis et al. | |
| 4,535,820 A * | 8/1985 | Raines | 137/854 |
| 4,683,916 A * | 8/1987 | Raines | 137/854 |
| 4,725,266 A * | 2/1988 | Siposs | 604/119 |
| 4,878,513 A * | 11/1989 | Ashby et al. | 137/102 |
| 4,935,010 A * | 6/1990 | Cox et al. | 604/122 |
| 5,242,411 A * | 9/1993 | Yamamoto et al. | 604/167.04 |
| 5,423,791 A | 6/1995 | Bartlett | |
| 6,039,302 A * | 3/2000 | Cote et al. | 251/149.1 |
| 6,482,188 B1 | 11/2002 | Rogers et al. | |
| 6,875,205 B2 | 4/2005 | Leinsing | |
| 6,979,323 B2 | 12/2005 | Rogers et al. | |
| 7,306,199 B2 | 12/2007 | Leinsing et al. | |

(Continued)

OTHER PUBLICATIONS

"Keeping I.V. therapy safe with needless systems", Nursing, Accessed Jun. 24, 2008.

(Continued)

*Primary Examiner* — Kevin C Sirmons
*Assistant Examiner* — William Carpenter

(57) ABSTRACT

Embodiments of luer-type needle-free valve devices are disclosed. One of the novel aspects of the invention is its ability to transform from an open state to a closed state. The open position eliminates the potential for a differential pressure to exist between the volume connected to the inlet and outlet of the valve fitting. The closed position enables the device to maintain a differential pressure between the volume connected to the inlet and outlet of the valve fitting. The invention is useful in manufacturing sterile medical devices by allowing all surfaces to communicate with the sterilizing agent when the valve is in an open configuration when it is in a closed position.

18 Claims, 7 Drawing Sheets

(56) References Cited

U.S. PATENT DOCUMENTS

| | | | |
|---|---|---|---|
| 7,319,735 | B2 | 1/2008 | Defreitas et al. |
| 7,785,299 | B2 * | 8/2010 | Crawford et al. ............. 604/246 |
| 2004/0073171 | A1 | 4/2004 | Rogers et al. |
| 2004/0124389 | A1 * | 7/2004 | Phillips ...................... 251/149.4 |
| 2004/0158211 | A1 | 8/2004 | Rogers et al. |
| 2005/0148994 | A1 | 7/2005 | Leinsing |
| 2005/0194047 | A1 * | 9/2005 | Bausmith, III ................ 137/512 |
| 2006/0155258 | A1 | 7/2006 | Rogers et al. |
| 2006/0192164 | A1 | 8/2006 | Korogi et al. |
| 2006/0253090 | A1 | 11/2006 | Bradley et al. |
| 2006/0276770 | A1 | 12/2006 | Rogers |
| 2007/0083162 | A1 | 4/2007 | O'Reagan et al. |
| 2007/0156112 | A1 | 7/2007 | Walsh |
| 2007/0260104 | A1 | 11/2007 | Bretz |

OTHER PUBLICATIONS

"Brachytherapy", Radiology Info, Accessed May 28, 2008.

"About Brachytherapy: What is Brachytherapy", American Brachytherapy Society, Accessed May 28, 2008.

"Brachytherapy", Wikipedia the free enclyclopedia, Accessed May 28, 2008.

Material Comparison Chart, Date unknown.

"Overview of Sterilization Procedures", Medical Device Link, Accessed Dec. 22, 2008.

"ETO Sterilization", Medical Device Link, Accessed Nov. 8, 2007.

DuPONT Medical Packaging Technical Reference Guide, (Jan. 2007).

* cited by examiner

LUER-TYPE NEEDLE-FREE VALVE FITTING WITH BYPASS

FIELD

This patent specification is in the field of medical valves and specifically needle-free valves.

BACKGROUND

Over the years a wide variety of devices and methods have been developed to assist the health care practitioner in delivering medications, taking of body fluids and connecting medical devices. In more recent times, such devices and methods have been developed to not only assist the health care practitioner, but to also protect the health care practitioner and patients from needle sticks. Many of these devices and methods were also developed to work in a multifunctional manner with many different types of additional devices. Thus, a need remains for valve devices that may be used in fluid or gas flow and the transfer of fluids from medicinal containers, vials, bags and tubing to ports in other administrative structures for medical purposes.

Aside from the hazards of needle sticks from normal needle syringe transfers from medicinal vials to ports, there exists a common problem of reversal of fluid flow. Such a reversal of liquid flow through tubing occurs due to back pressure or leakage of the valves when used with medicinal containers such as bottles or vials. The luer-type needle free valve device for fluid transfer, however, is able to accomplish these procedures to enable a health care professionals trained in formulation and performing patient care to obtain the necessary quantity of volumes in an uncontaminated state from a manufacturer's container, to then transfer a quantity of fluid or gas to a port without the use of needles or the hazard or danger of leakage from the device valve in either direction, i.e. leakage of the fluid from the port on either side of the valve due to back pressure or leakage of medicinal fluid from the vial, bottle or syringe.

Earlier types of valve devices used multiple purpose adapters having a valve positioned in the closed position by a spring. The spring in these devices was overridden by insertion of a needleless syringe tip against the valve, overcoming the spring load thus opening the valve. These valves can then be used to push fluids or gases into port systems such as bottles, vials, bags and tubing to act as a channel between the port systems and needleless syringe for obtaining the fluids or gases from the system. The needle-free valve device can be opened and closed to inject or withdraw fluids or gases. Such valve devices accommodate various uses in supplier containers and hospital settings.

Embodiments of luer-type needle-free valves are those where the valves can be opened using a needleless syringe, tubing or device. Syringes, tubing and devices such as these have had the needle removed so that the interfacing end has only the luer taper or luer lock. Typically, the state of the art in needle-free valves are known as Luer-Activated Devices. Embodiments of the Luer-Activated Device may control a valve that prevents the outflow of fluid or gas through the connector until a standard luer connector is inserted, allowing the valve to open and fluid or gases to be inserted or withdrawn. Three types of Luer-Activated Devices are known in the art. The first of these are capped Luer-Activated Devices requiring a cap to be attached to the valve when the valve is not in use. These types of devices are difficult to maintain aseptically because contamination can easily occur during manipulation, and the open luer connection is difficult to swab. The second type of Luer-Activated Device is the Capless Luer-Activated Device. Such devices don't require capping between uses and use positive-pressure to open and close the valve when attaching and disconnecting the valve. The third type of Luer-Activated Device is a positive fluid displacement Luer-Activated Device that is similar to the Capless Luer-Activated Device in the means by which they are used, except that they may expel fluid or gas when they are disconnected.

Each of the aforementioned devices suffer numerous disadvantages. For example, they consist of a valve fitting that is normally closed when not attached to a syringe. However, when a syringe is attached to the valve, it displaces a diaphragm plunger that opens the valve enabling the syringe to deliver liquids, gases or other flowable materials to the volume connected to the valve fitting outlet. One of the limitations of these devices is that the valve fitting is in a closed configuration during manufacturing, sterilization and packaging. Thus, if the outlet of the valve fitting were connected to a sealed volume such as a syringe, it would present a sterilization problem because sterilization agents would not have reached all surface areas of the valve fitting during the sterilization procedure before or after packaging. In addition, in pressurized sterilization systems, a valve fitting attached to a syringe would compound sterilization problems or other situations where atmospheric pressure differs internally and externally resulting in damage to the valve. The differences in pressure occurring when the volume connected to the valve fitting outlet and/or nearby structures expands or contracts. Such damage only being discovered at the point of use.

Needle-free valves are also typically used in manufacturing sterile medical devices. Such medical devices use luer valves to hermetically connect two volumes. A common application is the connection between vials, bottles, bags, tubing, needles, and syringes. During manufacturing of such devices it is often necessary for the outlet and inlet of a valve fitting to communicate so that fluid sterilizing agents reach all surfaces of the device and the volumes they connect. Often times such sterilization procedures are aided by placing the device in a vacuum chamber to assist in drawing fluid sterilization agents into the device through the valve. When used in this manner, the configuration of a luer type device in clinical use differs because it is common for the outlet and inlet to be held closed, thus permitting the user to develop a differential pressure between the volumes at the outlet and the inlet. In view of this, it is evident that a manufacturer's interests to maintain the valve in an open position does not coincide with the clinician's interests to maintain the valve in a closed position. For example, when the manufacturer attempts to sterilize a closed valve device with a gaseous sterilizing agent, the agent does not reach all of the surfaces of the device. And any vacuum environment used in the sterilizing environment will cause an undesired expansion of the volume connected to the fitting outlet, which may ultimately result in the connected volume rupturing and the end user receiving a non-sterile product that may be damaged. In addition, this undesired expansion of the connected volume may damage the product packaging thereby voiding the sterile barrier.

As discussed above, no device exists in the state of the art that compensates for this problem. The present invention solves these and other possible problems of conventional devices, and relates to a luer-type needle free valve device or adapter for use with fluid or gaseous flow and administration structures for medical purposes.

Further, the present invention provides a device that fulfills both the manufacturer's interests as well as the clinician's interests by providing a self contained valve that acts both as a normally open valve during sterilization and normally closed valve during use.

SUMMARY OF DISCLOSURE

In general terms, embodiments of the invention are directed to a valve fitting having a valve assembly with a valve body. The valve body has a first end and a second end. The valve body defines a primary passageway and a secondary passageway between the first and second ends. A diaphragm within the primary passageway is also provided. The diaphragm may be in an open position and a closed position and may be flexible. When the diaphragm is in the open position, the primary passage way is open and the secondary passageways is closed. When the diaphragm is in the closed position, the primary passageway is closed and the secondary passageway is open depending on the position of the collars. In addition, a collar is slidably disposed around the first end. When the collar is in the first position, the secondary passageway is open, and when the collar is in a second position the secondary passageway is closed.

More specifically, embodiments of the invention are directed to a needle free valve fitting having a valve assembly with a valve body comprising an inlet, a plunger, and an outlet. In some embodiments of the invention the body also defines a primary passageway and secondary passageway between the inlet and outlet where the plunger may be moveable within the inlet. Additionally, a diaphragm exists within the primary passageway between the inlet and outlet. The diaphragm may open in response to movement of the plunger. When the diaphragm is open, the primary passageway is open and the secondary passageway is closed. When the diaphragm is closed, the primary passageway is closed and the secondary passageway maybe open or closed. In such embodiments, a collar is slideably disposed around the inlet. When the collar is in a first position, the secondary passageway is open, and when the collar is in a second position, the secondary passageway is closed.

Needle free valve fittings such as these relate to multipurpose devices that are adaptable to multiple medical use and device requirements. Such devices are suitable for use with ports, bags, medicine bottles, syringes or vials and lock connectors as well as needle free connectors. Other embodiments of the valve fitting are used in obtaining fluids such as diluents for use medications from vials and delivering to ports, other vials, bags, and tubing through use of needle free transfer systems having the adapter valve device in place. Still other embodiments of this device may be used with medical devices that require a connection port that must be closed during use, but open during packaging and sterilization.

Embodiments of the invention also generally relate to methods of sterilizing a device using sterilization agents defined as fluids that includes liquids, gases or other flowable materials. Such methods allow for the passage of a fluid sterilization agent through and around all surface areas of the needle free valve. Specifically, these methods allow the fluid sterilization agent to come in contact with all exposed surface areas in the primary and secondary passageways that are defined by the valve body, inlet, plunger, outlet, diaphragm, collar, as well as any additional parts of the valve.

The ethylene oxide sterilization process works by exposing the sterilization chamber's load (the medical devices or products) to ethylene oxide gas which inactivates any microorganisms present on the product thereby ensuring the product is sterile. There are four basic phases of an ethylene oxide sterilization cycle: 1. air removal, 2. steam injection, 3. ethylene oxide injection, 4. gas purge and air inbleed. The "air removal" phase of the process is the part of the sterilization process that causes problems for devices with sealed cavities.

Additional means of gas sterilization use plasma/hydrogen peroxide gas, ozone and chlorine dioxide. While other methods of sterilization include: radiation and e-beam processes, pulsed UV light, x-ray and gamma irradiation, electron beam, steam and heat processes, autoclaves and dry heat. Each of which may be combined or performed separately.

BRIEF DESCRIPTION OF THE DRAWINGS

FIG. 1 provides a representative embodiment of the invention, however, other embodiments of the invention may have differing shapes, sizes and means for connecting to other devices, bottles, vials, tubing and needles.

FIG. 2 provides a representative embodiment of the internal layout of the needle-free valve. In other embodiments of the invention, the layout of the device may have differing shapes, sizes, O-rings and diaphragms.

DETAILED DESCRIPTION OF PREFERRED EMBODIMENTS

Referring now in detail to the figures in which like numerals refer to like or corresponding elements among the seven figures. The needle free valve may be embodied in different configurations and is not limited to any of those configurations disclosed.

Figure 1:
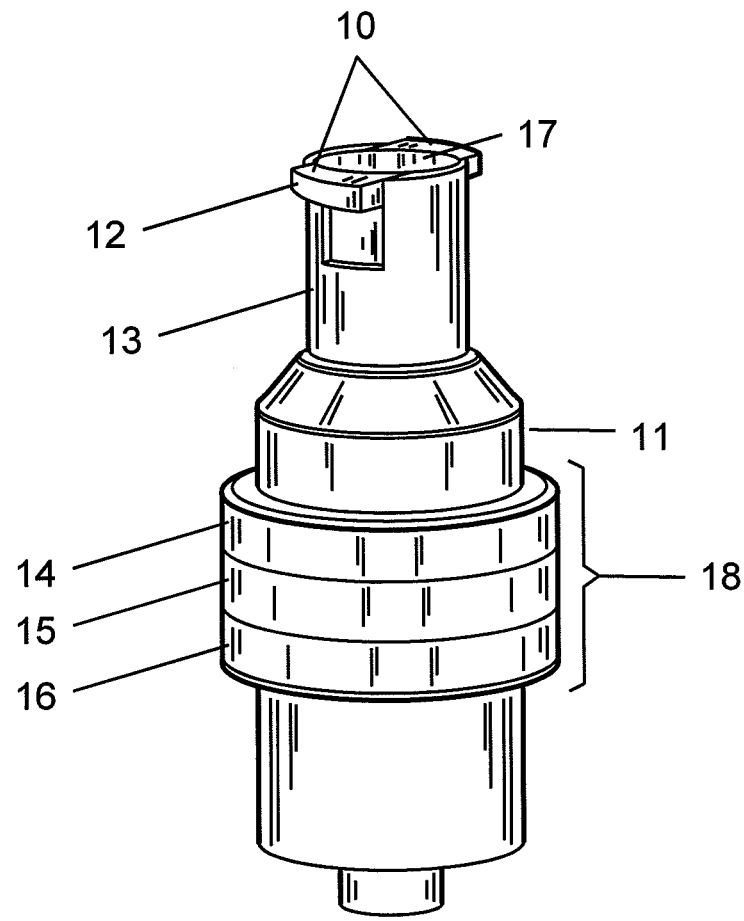
FIG. 1 illustrates a side view of one embodiment of a needle-free valve in the second position that incorporates embodiments of the present invention.

Illustrated in FIG. 1 is a side external view of an embodiments of a needle-free valve that includes various aspects of the present invention. Other embodiments may have differing shapes, sizes and points of connection. The particular configuration of FIG. 1 as well as all of the figures is for illustration purposes only. Specifically FIG. 1 presents an embodiment of a needle-free valve 11 having luer feature 12 that is slidably dispose within a collar 13. The luer feature defines an inlet 17 with a lip 10 used for interfacing with medical devices not limited to syringes, bottle, tubing, ports and catheters. The luer feature 12 may be a female port. The collar 13 is slidably disposed around the luer feature 12. The body 18 may be formed from an upper body portion 14, a middle body portion 15 and a lower body portion 16. The lower body portion 16 forms the outlet, that in this case may be a male port. Such a lower body portion 16 may be have differing configurations and sizes. The lower body portion 16 may also contain threads for attaching screw type devices as well as additional attachment devices (the threads are not visible in FIG. 1). The upper body portion 14, middle body portion 15 and lower body portion 16 may be made from the same or different materials and may be made from the same or different materials as the luer feature 12 or the collar 13, both of which may be made of the same or different materials as each other and the other portions of the body. Representative materials from which the upper body portion 14, middle body portion 15, lower body portion 16, luer feature 12 and collar 13 are made include: The materials used to construct the above can be any of a number of commodity or engineering plastics (e.g. polyethylene, polycarbonate, polyamide, PVC, acrylic, polypropylene, PET, polytetrafluoroethylene (PTFE), glass-filled PTFE, ethylene polypropylene, flourosilicone, etc.) or metals (aluminum, titanium, stainless steel, etc.) used in similar medical device applications and products.

Figure 2:
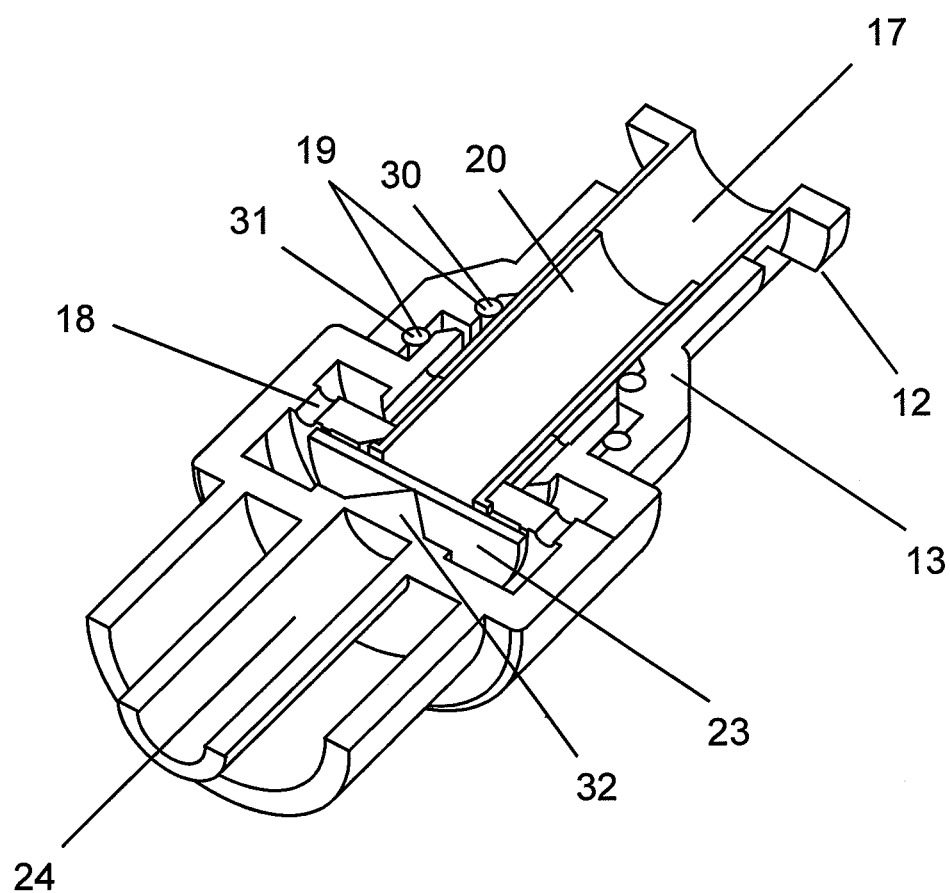
FIG. 2 illustrates a cross section view of one embodiment of a needle-free valve in the second position.

FIG. 2 is a cross-section view of an embodiment of a needle-free device with the collar 13 in the second position. Here, the luer feature 12 is set forth within the slidably disposed collar 13. Within the center of the luer feature 12 is the inlet 17. The inlet 17 may be of various sizes that allow its connection with differing types of ports, bottles, bags, tubing and syringes. The inlet 17 comprises a luer feature 12 and a diaphragm plunger 20. Within the inlet 17, the cylindrical diaphragm plunger 20 is hollow and may extend the entire length or partial length of the inlet 17 and may or may not contain a vent. The disclosure of the plunger 20 in FIG. 2 is for illustrative purposes only and is not meant to define the length of the plunger 20. The diaphragm plunger 20 may be of various diameters and lengths and may be made of the same or different materials as the additional parts of the device. The collar 13 is slidably displaced about the luer 12 and may possess one or more O-rings 19 that provide a sealing interface between the collar 13 and the luer 12. The O-rings 19 may also form a sealing interface between the collar 13 and the upper body portion 14. The O-rings are preferably made of any number of elastomers or rubbers (e.g. Buna-N, Viton, Silicone, Neoprene, etc,). When the collar 13 is in the first position, a primary O-ring 30 may form a sealing interface between the collar 13 and the luer 17 while the secondary O-ring 31 does not form a sealing interface between the collar and the upper body portion 14, thus allowing passage of fluid through the device. When the collar 13 is in the second position, a primary O-ring 39 forms a sealing interface between the collar 13 and the luer 17 while the secondary O-ring 31 forms a sealing interface between the collar and the upper body portion 14, thus preventing the passage of gas or fluid through the device.

Figure 6:
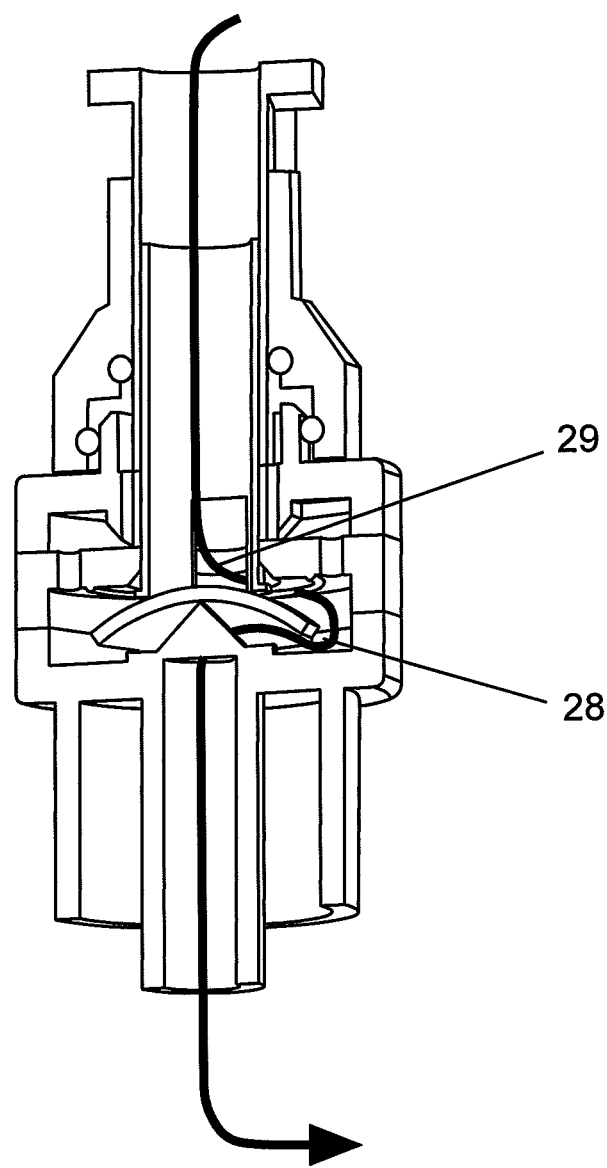
FIG. 6 illustrates a cross section of one embodiment of a needle-free valve in the second position outlining flow though the primary passageway. Additional representative embodiments in the second position may have differing shapes and sizes. Additional embodiments also may conform to the first position and result in a differing shape and size of the device in the second position.

In certain embodiments of the invention such as the embodiment shown in FIG. 6, the diaphragm plunger extends beyond the base of the luer 12 and through the upper body portion 14 and the middle body portion 15. The diaphragm plunger may be slidably disposed within the luer 12, the upper body portion 14 and the lower body portion 16. In other embodiments such as the embodiment shown in FIG. 7, the base of the diaphragm plunger 20 rests on the diaphragm 23 that extends outward beyond the diameter of the diaphragm plunger. The diaphragm 23 is circular in certain embodiments, but may also be formed in other shapes as necessary to function appropriately. The diaphragm 23 rests against the portion of the middle body portion 15 closest to the lower body portion 16. The diaphragm does not extend to the outer edge of the middle portion of the body in order to allow the secondary passageway 27 to remain in the open position. In other embodiments, however, the diaphragm 23 may extend to the outer edge of the middle portion 15 of the body. The diaphragm 23 is supported by diaphragm support 32 which is preferably angled as shown in FIG. 2. The diaphragm is preferably made from an elastomer or rubber (e.g. silicone). These materials in no way limit the type of material that may form the diaphragm. The diaphragm support 32 is formed by a portion of the lower body portion 16 that traverses the outlet 24.

In certain embodiments, the lower body portion 16 is circular in nature and contains an outer ring and inner male port. The inner male port forms the fluid outlet of the valve. The outer ring of the lower body portion 16 may contain threads to assist in interfacing with devices that may connect to the male port.

The middle body portion the embodiment shown in FIG. 2 contains a fluid bypass 18 that runs perpendicular to the plane of the middle body portion 15. This fluid bypass 18 allows flow from the upper body portion 14 through middle body portion 15 to the lower body portion 16 and vice versa. In other embodiments of the invention, however, the fluid bypass 18 may possess differing configurations in order to form a bypass. The fluid bypass 18 may be located at the outer edge of the diaphragm 23 and is in the form of hollow tubes traversing the plane of the of the middle body portion 15. The fluid bypass 18 may be of any shape and size to permit fluid passage.

Figure 3:
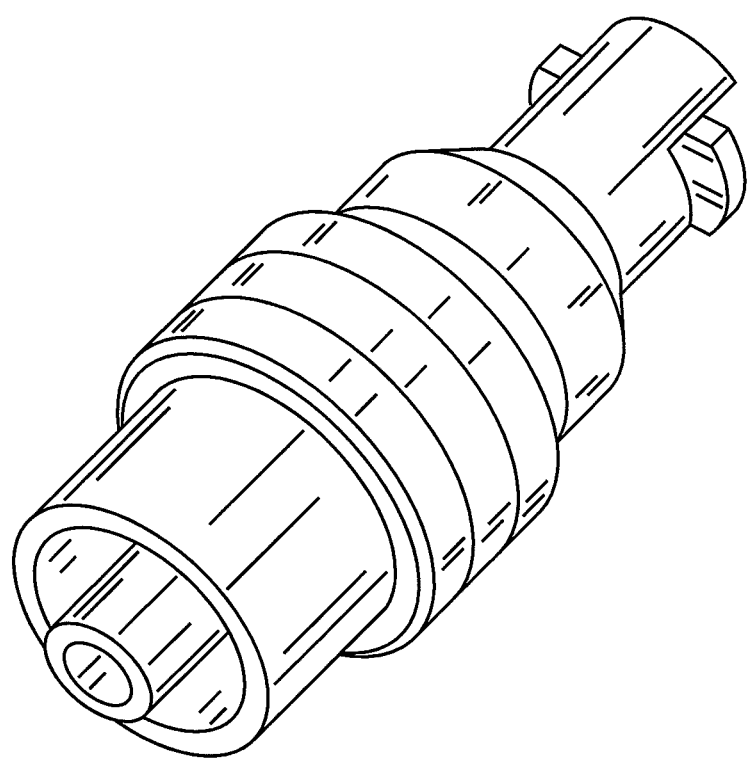
FIG. 3 illustrates a perspective view of one embodiment of a needle-free valve in the first position. Additional representative embodiments in the first position may have differing shapes and sizes. Additional embodiments also may conform to the first position and results in a differing shape and size of the device in the first position.

FIG. 3 is a perspective view of a needle-free device embodiment of the present invention with the collar 13 in the first position. When the collar 13 is in the first position, the collar 13 is extended toward the luer feature 12 away from the upper body portion 14. FIG. 3 also provides a view of the fluid outlet 24 wherein the male port is centered. In certain embodiments, FIG. 3 is representative of a normally open state of the device. In this position, the valve may be sterilized allowing fluid sterilization agents to contact the surfaces of the valve. While the embodiment represented by this FIG. 3 does not contain threads on any portion of the male port, other embodiments may possess threads on the male port.

Figure 4:
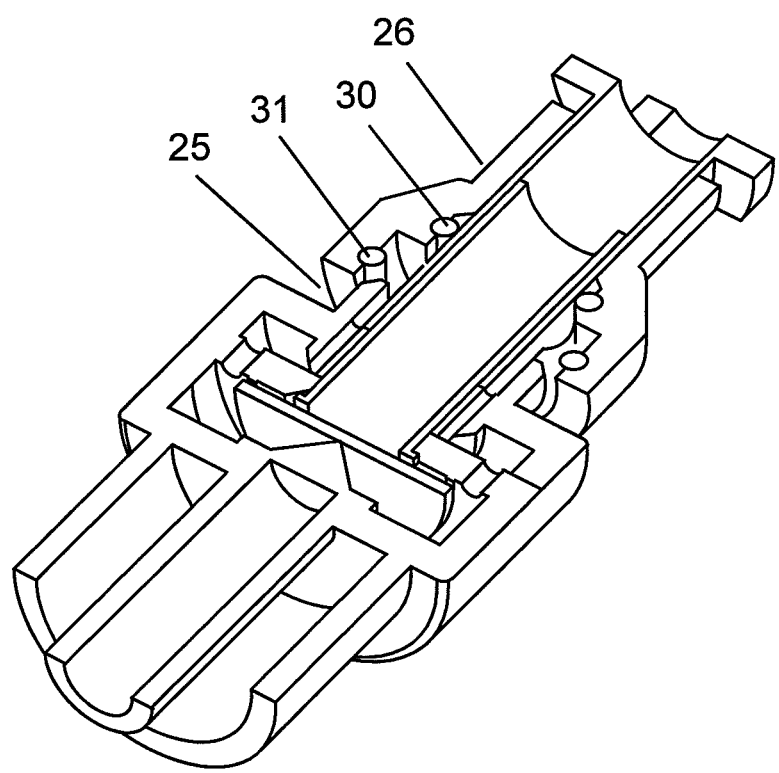
FIG. 4 illustrates a cross-section view of one embodiment of a needle-free valve in the first position. Additional representative embodiments in the first position may have differing shapes, sizes O-rings and diaphragms. Additional embodiments also may conform to the first position and results in a differing interfaces between the O-rings and diaphragms of the device.

FIG. 4 is a cross section view of an embodiment of the needle free valve with the collar 13 in the first position. With the collar 13 extended toward the luer feature 12, a fluid bypass exhaust 25 exists at the opening between the collar 13 and the upper body portion 14. The size of the fluid bypass exhaust 25 may vary depending of the type of exhaust that requires venting. In the first position an embodiment of the invention may posses a primary O-ring 30 that interfaces the collar while the secondary O-ring 31 does not interface with the upper body portion 14. Such an embodiment differs from an embodiment in the second position where the secondary O-ring 31 would interface with the upper body portion 14.

While in the first position, the primary O-ring 31 may form a seal at its interface with the collar 13 thereby forming a fluid bypass exhaust 25 in the device.

Figure 5:
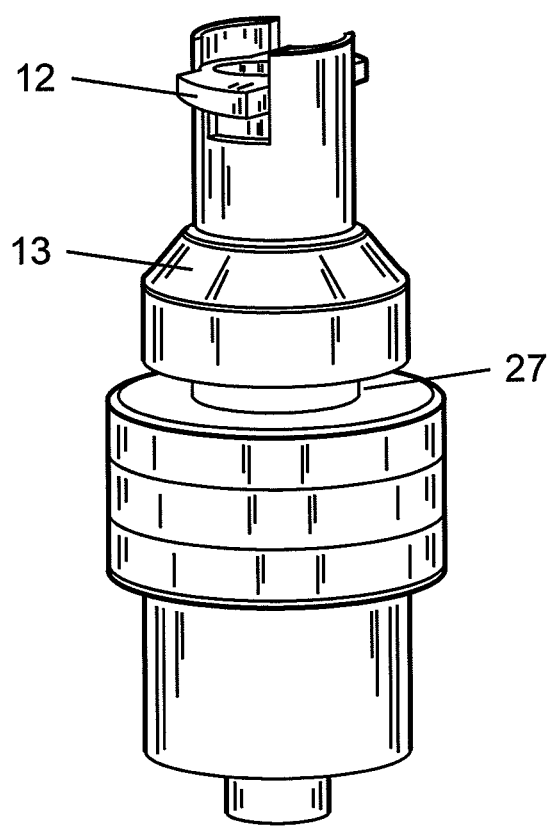
FIG. 5 illustrates a side view one embodiment of a needle-free valve in the first position that incorporates aspects of the present invention. Additional representative embodiments in the first position may have differing shapes and sizes. Additional embodiments also may conform to the first position and results in a differing shape and size of the device.

FIG. 5 is a side view of an embodiment of a needle-free device with the collar 13 in the first position extended toward the luer feature 12 away from the upper body portion 14. FIG. 5 demonstrates that the collar 13 may extend beyond the luer feature 12 in the first position. The view of the fluid bypass 27 is also shown and may extend around the circumference of the upper body portion 14. Other embodiments may provide for differing vents for the fluid bypass 27.

FIG. 6 provides a cross-section view of an embodiment of a needle-free valve with the collar in the first position demonstrating flow through the primary passageway 28. This figure is an example of an embodiment demonstrating that when a syringe or device is connected at the luer, the collar 13 will be in the first position to seal the-off the fluid bypass exhaust 25. FIG. 6 also provides an embodiment demonstrating a configuration that may exist when the valve is depressed by a syringe, port or tubing is attached to the luer 12 that would depress the plunger 17 and deflect a diaphragm 23. Such a configuration allows flow around the diaphragm 23 and through the device and through the primary passageway 28.

In FIG. 6, flow through the primary passageway occurs when fluid enters the inlet 17 at the luer traveling through the hollow diaphragm plunger 20 and then through a vent 20 on the diaphragm plunger 29 that may extend from the base of the diaphragm plunger 20 to the upper body portion 14. When the diaphragm 23 is depressed, the vent 29 forms a passage that is bounded by the diaphragm plunger 23, middle body portion 15 and diaphragm 23. After passage through the vent 29 the flow is contained in volume defined by the middle body portion 15 and lower body portion 16. Flow may then travel through the top portion of the outlet in the lower body portion 16 and finally through the outlet 24 on the male port of the lower body portion 16.

When a syringe or device is removed, the combination or individual activity of positive down stream pressure and the native state of the diaphragm 23 result in the diaphragm plunger 20 moving toward the outlet 24 closing the primary passageway 28 to fluid flow.

Figure 7:
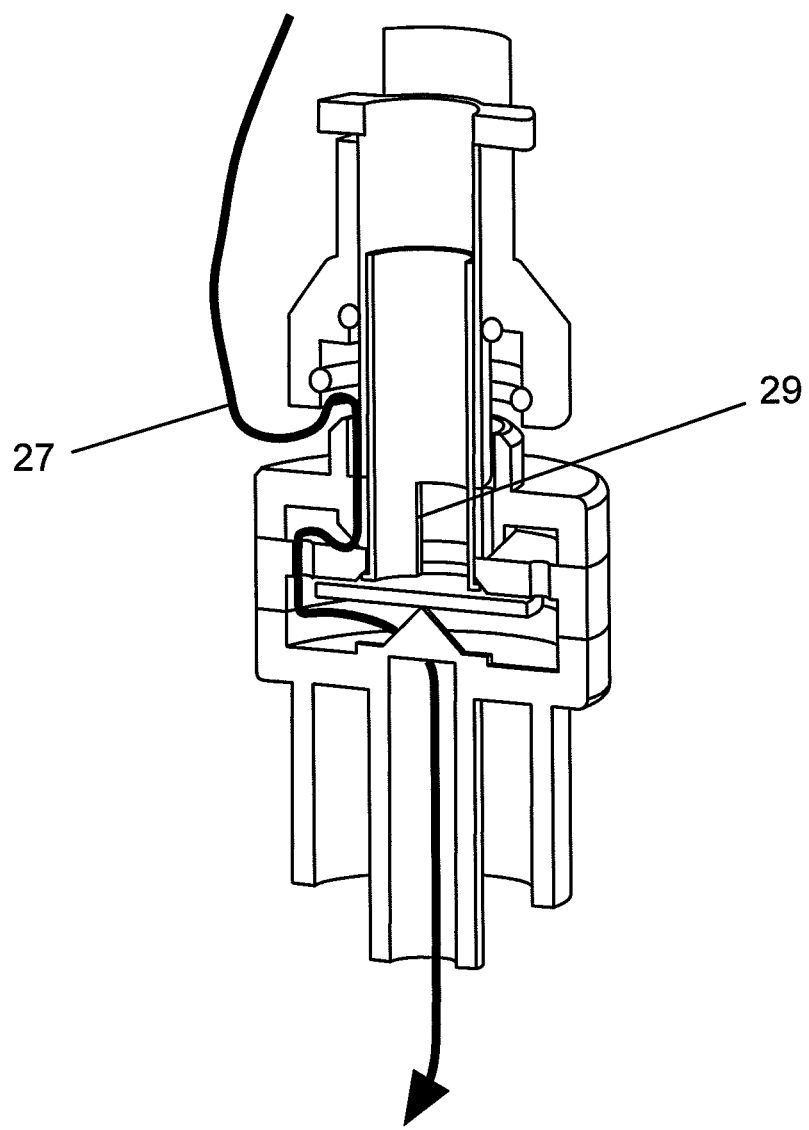
FIG. 7 illustrates a cross-section view of one embodiment of a needle-free valve in the first position outlining flow through the secondary passageway. Additional representative embodiments in the first position may have differing shapes, sizes O-rings and diaphragms. Additional embodiments also may conform to the first position and results in a differing interfaces between the O-rings and diaphragms of the device.

FIG. 7 provides an embodiment disclosing a cross section view of a needle-free valve with the collar 13 in the second position demonstrating flow through the secondary passageway 27 when the primary passageway 28 is closed. This figure demonstrates that when a syringe or device is not connected at the luer, the collar 13 will be in the second position opening the fluid bypass exhaust 25. In this position, a syringe or device may not be attached at the luer 12 and as a result, the diaphragm plunger 20 may not be depressed resulting the primary passageway 28 being closed.

In FIG. 7, flow through the secondary passageway occurs first by entering the fluid bypass 18 then traveling through the inside of the collar 13 on the upper body portion 14 that extends around the circumference of the lower body portion 16 of the needle free valve. At the base of the luer that interfaces with the upper body portion 14, flow then proceeds through individual passageways that extend through the upper body portion 14 into a chamber formed by the upper body portion 14 and middle body portion 15. Flow from this chamber then proceeds through the a passageway formed by the middle body portion 15 into a volume defined by the middle body portion 15 and lower body portion 16. Flow may then travel through the top portion of the outlet in the lower body portion 16 and finally through the outlet 24 on the male port of the lower body portion 16. Flow may also proceed in the opposite direction. This description of flow is not meant to limit the direction or type of flow through the device.

Additional embodiments of this invention may be defined as a valve fittings that may possess a valve assembly having a valve body 18. The valve body 18 comprises a first end and a second end and also comprise a primary passageway 28 and a secondary passageway 27 between the first and second ends. The embodiments of this invention also may possess a diaphragm 23 within the primary passageway 28. The diaphragm 23 may be in an open position or a closed position. When the diaphragm 23 is in the open position, the primary passageway 28 is open and secondary passageway 27 is closed. However, when the diaphragm is in the closed position, the primary passageway 28 is closed and the secondary passageway 27 may be open depending on whether the collar 13 is in a first or second position. As described above, embodiments of this invention also possess a collar 13 slidably disposed around the first end. When the collar is in a first position the secondary passageway is open, and when the collar is in a second position the secondary passageway is closed.

In other embodiments, the needle free valve fitting may comprise a valve assembly with a valve body 18. The valve body 18 in this embodiment may possess an inlet 17, a plunger 20, and an outlet 24. The valve body 18 also defines a primary passageway 28 and secondary passageway 27 between the inlet 17 and outlet 24. This embodiment also may possess a plunger 20 that is moveable within the inlet 17. Such embodiments also may possess a diaphragm 23 within the primary passageway 28 between the inlet 17 and outlet 24. In this embodiment, the diaphragm 23 opens in response to movement of the plunger 20, and when the diaphragm 23 is open, the primary passageway 28 is open and the secondary passageway 27 is closed. As described in other embodiments, when the diaphragm 23 is closed the primary passageway 28 is closed and the secondary passageway 27 may be open depending on whether a collar 13 is in the a first or second position.

In certain embodiments of the invention the collar may possess O-ring seals 19 at the interface of the body and collar. Additionally, certain embodiments contain a diaphragm that may be positioned between the plunger and a diaphragm support 32. In these embodiments, the plunger may contain a vent 30 as shown in FIG. 6. Theses embodiments also have a first end that comprises a luer for device attachment.

An additional embodiment of the invention includes a method of sterilizing a device in a manner where differential pressure will not exist between the inlet 17 and outlet 24 of the device. This method includes providing a needle free valve fitting that has a valve assembly with a valve body 18. The valve body comprising an inlet 17, a plunger 20 that moves in within the inlet 17, and an outlet 24. The valve body 18 defines a primary passageway 28 and secondary passageway 27 between the inlet 17 and outlet 24. The needle free valve fitting used in the method may also possesses a diaphragm 23 in the primary passageway 28 between the inlet 17 and outlet 24 where the diaphragm 23 opens in response to movement by the plunger 20. Movement of the plunger 20 may open or close the diaphragm 23 so that when the diaphragm is open, the primary passageway 28 is open and the secondary passageway 27 is closed. When the diaphragm 23 is closed the primary passageway 28 is closed and the secondary passageway 27 may be open depending on whether the collar 13 in the first or second position.

The active step in the method would consist of exposing the needle free valve fitting to a fluid sterilization agent that will be in communication with surface areas such as the body 18, the inlet 17 and outlet 24, the plunger 20, the primary passageway 28 and secondary passageway 27, the diaphragm 23 and collar 13. When the fluid sterilization agent is exposed to the needle free valve fitting, the diaphragm 23 may be open or closed and the collar 13 may be in a first or second position.

The fluid sterilization agent may be ethylene oxide as encompassed by embodiments of the claimed invention. However, additional means of gas sterilization use plasma/hydrogen peroxide gas, ozone and chlorine dioxide. While other methods of sterilization include radiation and e-beam processes, pulsed UV light, x-ray and gamma irradiation, electron beam, steam and heat processes, autoclaves and dry heat. Each of which may be combined or performed separately.

The use of ethylene oxide is the state of the art in sterilization in the device field. The relatively low process temperature (in comparison to steam sterilization) has made ethylene oxide sterilization an excellent method for many products.

The methylating properties of ethylene oxide makes it an ideal sterilizing agent. This property, however, also makes it extremely dangerous at ambient oxygen levels. To ensure an intrinsically safe environment for the ethylene oxide, a set of evacuations coupled with steam additions is executed at the start of every sterilization procedure. Ethylene oxide gas is then added and allowed to sit with the product being sterilized. During this point in the method, the ethylene oxide comes in contact with all of the surface areas of the valve fitting. During this "sitting phase" or "gas dwell phase" the product and its packaging absorb ethylene oxide gas. Following the gas dwell phase, a series of evacuations and air infusions occur. This helps in the removal of gas from the product. The product is then transferred to an aeration chamber where ethylene oxide and ethylene oxide degradation products dissipate safely from the product. Depending on the nature of the product and aeration conditions, this gas dissipation period may last from several hours to weeks and even months. When sterilization is complete, the gas is evacuated from the chamber and the product is removed.

A person skilled in the art will appreciate the foregoing as only illustrative of the principles of the invention, and that various modification may be to both the device and the methods of sterilizing the device presented without departing from the scope and spirit of the invention.

What is claimed is:

1. A valve comprising:
a valve assembly having a valve body, wherein said body comprises a first end and a second end, said valve body defining a primary passageway and a secondary passageway between said first and second ends;
a diaphragm within said primary passageway, said diaphragm having an open position and a closed position;
a collar slidably disposed around said valve body, wherein said collar is in a first position said secondary passageway is open, and wherein when said collar is in a second position said secondary passageway is closed;
wherein when said diaphragm is in said open position, said primary passageway is open and said secondary passageway is closed, and wherein when said diaphragm is in said closed position, said primary passageway is closed and said secondary passageway is (i) open when the collar is in the first position and (ii) closed when the collar is in the second position.

2. The valve of claim 1, wherein said collar comprises at least one O-ring seal at the interface of the body and collar.

3. The valve of claim 1, wherein said diaphragm is positioned between a plunger and an angled diaphragm support.

4. The valve of claim 3, wherein said plunger contains a vent.

5. The valve of claim 1, wherein said first end is configured for device attachment.

6. The valve of claim 1, wherein said valve body comprises a fluid bypass.

7. A needle free valve fitting comprising:
a valve assembly having a valve body, said body comprising an inlet, a plunger, and an outlet, and defining a primary passageway and secondary passageway between said inlet and outlet, wherein said plunger is moveable within said inlet;
a diaphragm within said primary passageway between said inlet and outlet wherein said diaphragm opens in response to movement of said plunger, and
a collar slideably disposed around said inlet, wherein when said collar is in a first position said secondary passageway is open, and when said collar is in a second position said secondary passageway is closed;
wherein when said diaphragm is in said open position, said primary passageway is open and said secondary passageway is closed, and wherein when said diaphragm is in said closed position, said primary passageway is closed and said secondary passageway is (i) open when the collar is in the first position and (ii) closed when the collar is in the second position.

8. The needle free valve fitting of claim 7, wherein said collar comprises at least one O-ring seal at the interface of the body and collar.

9. The needle free valve fitting of claim 7, wherein said diaphragm is positioned between said plunger and an angled diaphragm support.

10. The needle free valve fitting of claim 7, wherein said plunger further comprises a vent.

11. The needle free valve fitting of claim 7, wherein said inlet is configured for device attachment.

12. The needle free valve fitting of claim 7, wherein said outlet comprises a connection port for device attachment.

13. The needle free valve fitting of claim 7, wherein said plunger is hollow.

14. The needle free valve fitting of claim 7, wherein said valve body comprises a fluid bypass.

15. A method of sterilizing a device comprising:
providing a needle free valve fitting comprising:
a valve assembly having a valve body, said body comprising an inlet, a plunger, and an outlet, and defining a primary passageway and secondary passageway between said inlet and outlet, wherein said plunger is moveable within said inlet;
a diaphragm within said primary passageway between said inlet and outlet and
a collar slideably disposed around said valve body, wherein when said collar is in a first position said secondary passageway is open, and when said collar is in a second position said secondary passageway is closed,
wherein said diaphragm opens in response to movement of said plunger, and wherein when said diaphragm is open said primary passageway is open and said secondary passageway is closed, and when said diaphragm is closed said primary passageway is closed and said secondary passageway is (i) open when said collar is in said first position and (ii) closed when said collar is in said second position;
exposing said needle free valve fitting to a fluid sterilization agent so that said fluid sterilization agent is in communication with surface areas comprising said body, said inlet and outlet, said plunger, said primary and secondary passageways, said diaphragm and said collar.

16. The method of claim 15, wherein said sterilization agent is ethylene oxide.

17. The method of claim 15, wherein a differential pressure does not exist between said inlet and said outlet.

18. A needle free valve fitting comprising:
- A valve assembly having a valve body, said body comprising an inlet, a plunger, a fluid bypass, and an outlet, and defining a primary passageway and secondary passageway between said inlet and outlet, wherein said plunger is moveable within said inlet;
- A diaphragm within said primary passageway between said inlet and outlet wherein said diaphragm deflects but is not penetrated in response to movement of said plunger;
- A diaphragm support in contact with said diaphragm; and
- A collar slideably disposed around said inlet, wherein where said collar is in a first position said secondary passageway is open, and when said collar is in a second position said secondary passageway is closed;
- wherein when said diaphragm is in said open position, said primary passageway is open and said secondary passageway is closed, and wherein when said diaphragm is in said closed position, said primary passageway is closed and said secondary passageway is (i) open when the collar is in the first position and (ii) closed when the collar is in the second position.

* * * * *